United States Patent
Bek et al.

(10) Patent No.: US 7,422,587 B2
(45) Date of Patent: Sep. 9, 2008

(54) SYSTEMS AND METHODS FOR TREATING TISSUE REGIONS OF THE BODY

(75) Inventors: Robin Bek, Campbell, CA (US); John W. Gaiser, Mountain View, CA (US); Scott H. West, Livermore, CA (US); Patrick Rimroth, San Jose, CA (US)

(73) Assignee: Respiratory Diagnostic, Inc., Redmond, WA (US)

( * ) Notice: Subject to any disclaimer, the term of this patent is extended or adjusted under 35 U.S.C. 154(b) by 344 days.

(21) Appl. No.: 11/114,592

(22) Filed: Apr. 26, 2005

(65) Prior Publication Data

US 2005/0187546 A1   Aug. 25, 2005

Related U.S. Application Data

(63) Continuation of application No. 10/857,632, filed on May 28, 2004, now abandoned, which is a continuation-in-part of application No. 09/955,915, filed on Sep. 19, 2001, now Pat. No. 6,699,243.

(51) Int. Cl.
*A61B 18/18* (2006.01)
*A61B 19/00* (2006.01)

(52) U.S. Cl. ................ 606/41; 128/898; 607/133
(58) Field of Classification Search ............ 606/41, 606/45–50, 192–194; 607/101–105; 128/898
See application file for complete search history.

(56) References Cited

U.S. PATENT DOCUMENTS

| | | | |
|---|---|---|---|
| 4,955,377 A * | 9/1990 | Lennox et al. | 607/105 |
| 5,957,962 A * | 9/1999 | Wallsten et al. | 607/104 |
| 6,006,755 A | 12/1999 | Edwards | |
| 6,044,846 A | 4/2000 | Edwards | |
| 6,056,744 A | 5/2000 | Edwards | |
| 6,092,528 A | 7/2000 | Edwards | |
| 6,254,598 B1 | 7/2001 | Edwards et al. | |
| 6,464,689 B1 | 10/2002 | Qin et al. | |
| 6,464,697 B1 | 10/2002 | Edwards et al. | |
| 6,514,249 B1 * | 2/2003 | Maguire et al. | 606/41 |
| 6,544,226 B1 | 4/2003 | Gaiser et al. | |
| 6,547,776 B1 | 4/2003 | Gaiser et al. | |
| 6,589,238 B2 | 7/2003 | Edwards et al. | |
| 6,645,201 B1 | 11/2003 | Utley et al. | |
| 6,699,243 B2 | 3/2004 | West et al. | |
| 6,733,495 B1 | 5/2004 | Bek et al. | |
| 6,783,523 B2 | 8/2004 | Qin et al. | |
| 6,790,207 B2 | 9/2004 | Utley et al. | |
| 6,802,841 B2 | 10/2004 | Utley et al. | |
| 6,827,713 B2 | 12/2004 | Bek et al. | |
| 6,971,395 B2 | 12/2005 | Edwards et al. | |

(Continued)

*Primary Examiner*—Michael Peffley
(74) *Attorney, Agent, or Firm*—Ryan Kromholz & Manion S.C.

(57) ABSTRACT

Systems and methods deploy a therapeutic or diagnostic element into contact with a body tissue region. The systems and methods can sense position of the therapeutic or diagnostic element relative to a targeted tissue region without direct or indirect visualization, by sensing fluid pressure in a fluid path having an outlet located at or near the therapeutic or diagnostic element. The systems and methods can also inflate the therapeutic or diagnostic element during use, while taking steps to avoid over-inflation and/or while dynamically monitoring the pressure conditions within the expanded element.

7 Claims, 14 Drawing Sheets

U.S. PATENT DOCUMENTS

2002/0151871 A1 10/2002 Gaiser et al.
2002/0162555 A1 11/2002 West et al.
2004/0089313 A1 5/2004 Utley et al.

* cited by examiner

SYSTEMS AND METHODS FOR TREATING TISSUE REGIONS OF THE BODY

RELATED APPLICATIONS

This application is a continuation of co-pending U.S. patent application Ser. No. 10/857,632, filed May 28, 2004 (now abandoned), which is a continuation-in-part of U.S. patent application Ser. No. 09/955,915, filed Sep. 19, 2001, now U.S. Pat. No. 6,699,243, which is incorporated herein by reference.

FIELD OF THE INVENTION

The invention is directed to devices, systems and methods for treating tissue regions of the body.

BACKGROUND OF THE INVENTION

Catheter-based devices that deploy expandable structures into interior body regions are well known. These structures are typically introduced through a body lumen or vessel in a collapsed, low profile condition. Once at or near the targeted body region, the structures are expanded in situ into an enlarged condition to make contact with tissue. The structures can carry operative elements that, when in contact with tissue, perform a therapeutic or diagnostic function. They can, for example, deliver energy to ablate targeted tissue in the region.

Some of these structures can be expanded by inflation by delivery of fluid into the interior of the structure. It is desirable to control the amount of inflation, so as not to over-inflate the structures. Over-inflation can lead to damage of the structure, or unintended trauma or damage to nearby tissue.

With structures that are expanded in situ, it is also desirable to ascertain whether the structure actually is in contact with the targeted tissue region. Absent such contact, the desired therapeutic or diagnostic outcome may not be achieved.

SUMMARY OF THE INVENTION

The invention provides improved systems and methods for treating a tissue region.

One aspect of the invention provides systems and methods for sensing the position of a therapeutic or diagnostic element with respect to a targeted tissue region. The systems and methods comprise a fluid path having an outlet located at or near the therapeutic or diagnostic element. The location of the outlet places the outlet into a position with respect to the targeted tissue region concurrently with the therapeutic or diagnostic element. The systems and methods also include a source of fluid under pressure. The source is in communication with the fluid path to convey fluid under pressure through the fluid path. The systems and methods include a fluid pressure sensor, which communicates with the fluid path to sense prevailing fluid pressure in the path. The systems and methods also include an output to indicate the sensed prevailing fluid pressure or changes in the sensed prevailing fluid pressure over time. The sensed pressure conditions correlate with the position of the therapeutic or diagnostic element relative to the targeted tissue region. In one embodiment, the source of fluid conveys air under pressure, and the fluid pressure sensor comprises a manometer.

According to this aspect of the invention, changes in tissue pressure at or near the path outlet governs fluid flow in the path and gives rise to changes in fluid pressure within the path. Changes in the prevailing fluid pressure can be correlated to the position of the path outlet relative to a targeted tissue region. This aspect of the invention makes possible the sensing of the position of a remote structure with respect to a targeted tissue region without direct or indirect visualization, or without other complicated electrical or mechanical paraphernalia.

Another aspect of the invention provides systems and methods for inflating an inflatable structure that carries a therapeutic or diagnostic element. The systems and methods comprise a source of fluid under pressure. A supply line communicates with the inflatable structure and the source to convey fluid into the inflatable structure to inflate the inflatable structure for use. The systems and methods include a pressure relief valve. The pressure relief valve communicates with the supply line. The pressure relief valve opens and vents fluid from the supply line when a predetermined pressure condition exists in the supply line. This pressure condition is indicative that a desired interior pressure exists within the inflatable structure. This aspect of the invention assures that the inflatable structure is not subject to over-inflation during use.

Another aspect of the invention provides systems and methods for dynamically monitoring pressure conditions within an inflatable structure that carries a therapeutic or diagnostic element. The systems and methods include a pressure sensing element that dynamically senses interior pressure within the inflatable structure and generates an output. The sensing can be accomplished in real time, with an appropriate output generated to provide visual or audible feedback to the operator, and/or provide automated process control feedback based upon the sensed pressure information. The use of a dynamic pressure sensing element makes possible the automated inflation of an inflatable body in a straightforward and reliable manner. The use of dynamic pressure monitoring and control also facilitates the use of a porous balloon structure. The porous balloon structure is inflated to a desired pressure condition by the delivery of a liquid, while a portion of the inflation liquid is discharged through pores in the balloon, to provide a desired flow of irrigation fluid to the tissue region concurrent with inflation.

Other features and advantages of the inventions are set forth in the following Description and drawings, as well as in the appended claims

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DETAILED DESCRIPTION OF THE PREFERRED EMBODIMENTS

This Specification discloses various catheter-based systems and methods for treating dysfunction in various locations in an animal body. For example, the various aspects of the invention have application in procedures requiring treatment of sphincters and adjoining tissue regions in the body, or hemorrhoids, or incontinence, or obesity, or restoring compliance to or otherwise tightening interior tissue or muscle regions. The systems and methods that embody features of the invention are also adaptable for use with systems and surgical techniques that are not necessarily catheter-based.

The systems and methods are particularly well suited for treating dysfunctions in the upper gastrointestinal tract, e.g., in the lower esophageal sphincter and adjacent cardia of the stomach. For this reason, the systems and methods will be described in this context. Still, it should be appreciated that the disclosed systems and methods are applicable for use in treating other dysfunctions elsewhere in the body, which are not necessarily sphincter-related.

I. Overview

Figure 1:
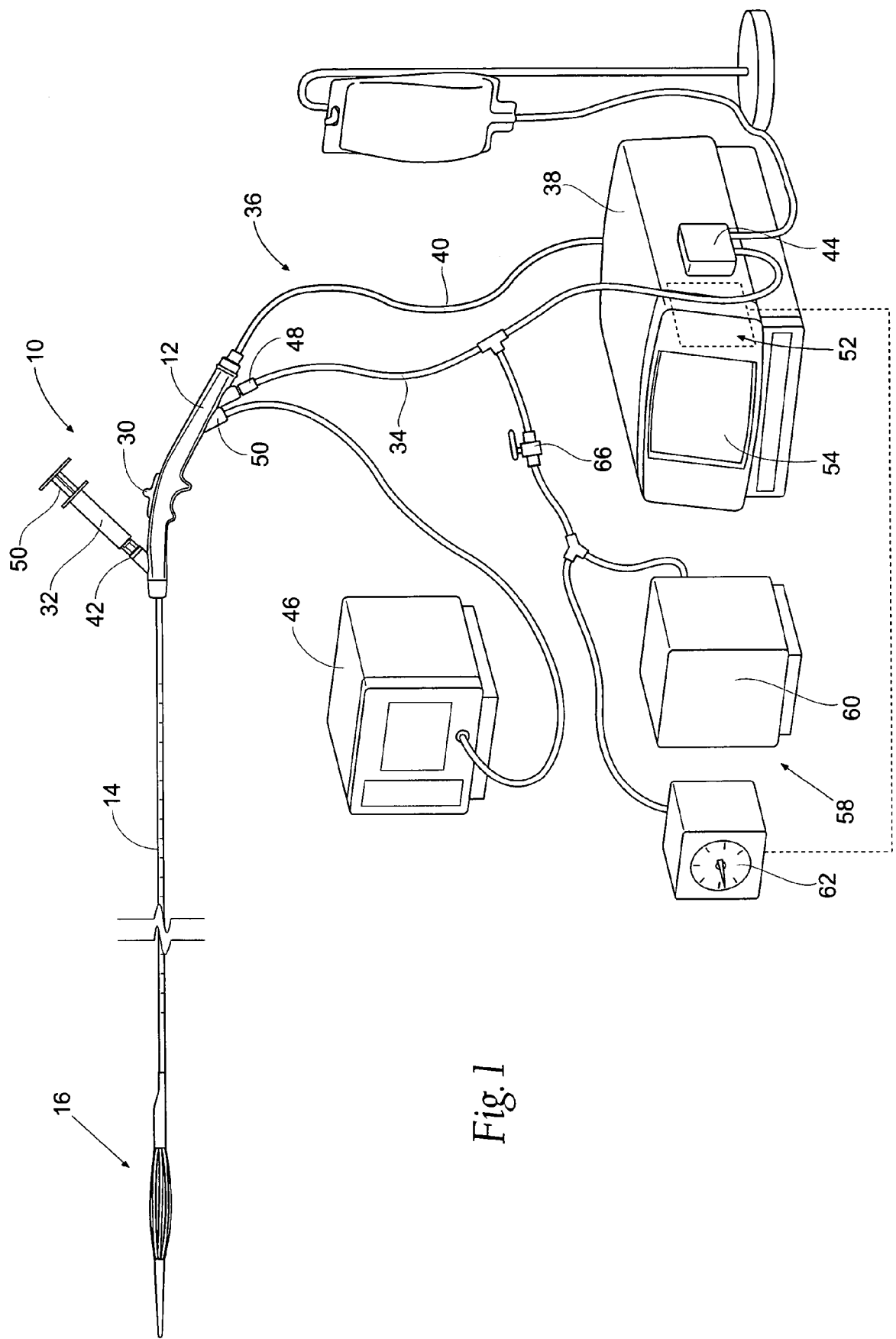
FIG. 1 is a schematic view of a system for treating tissue.

A tissue treatment device 10 and associated system 36 are shown in FIG. 1.

The device 10 includes a handle 12 made, e.g., from molded plastic. The handle 12 carries a flexible catheter tube 14 constructed, for example, by extrusion using standard flexible, medical grade plastic materials, like Pebax™ plastic material, vinyl, nylon, poly(ethylene), ionomer, poly(urethane), poly(amide), and poly(ethylene terephthalate). The handle 12 is sized to be conveniently held by a physician, to introduce the catheter tube 14 into the tissue region targeted for treatment. The catheter tube 14 may be deployed with or without the use of a guide wire.

The catheter tube 14 carries on its distal end an operative element 16. The operative element 16 can take different forms and can be used for either therapeutic purposes, or diagnostic purposes, or both. The operative element 16 can support, for example, a device for imaging body tissue, such as an endoscope, or an ultrasound transducer. The operative element 16 can also support a device to deliver a drug or therapeutic material to body tissue. The operative element 16 can also support a device for sensing a physiological characteristic in tissue, such as electrical activity, or for transmitting energy to stimulate tissue or to form lesions in tissue.

Figure 2:
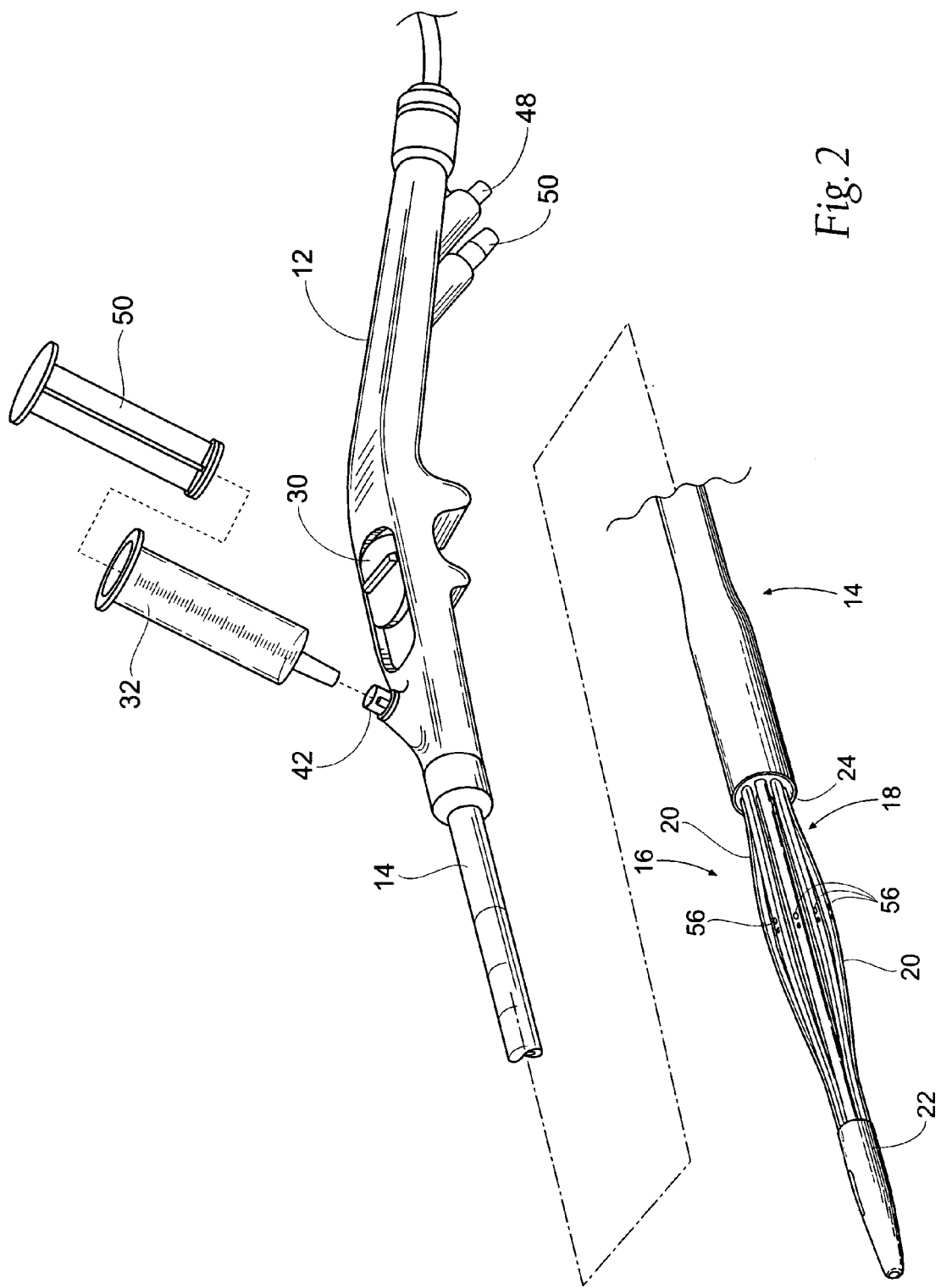
FIG. 2 is an enlarged view of the treatment device, with parts broken away and in section, that is associated with the system shown in FIG. 1, the treatment device comprising basket structure that carries selectively deployable electrode elements and that expands in response to inflation of an interior balloon structure, FIG. 2 showing the basket in a collapsed condition with the electrode elements retracted.
Figure 3:
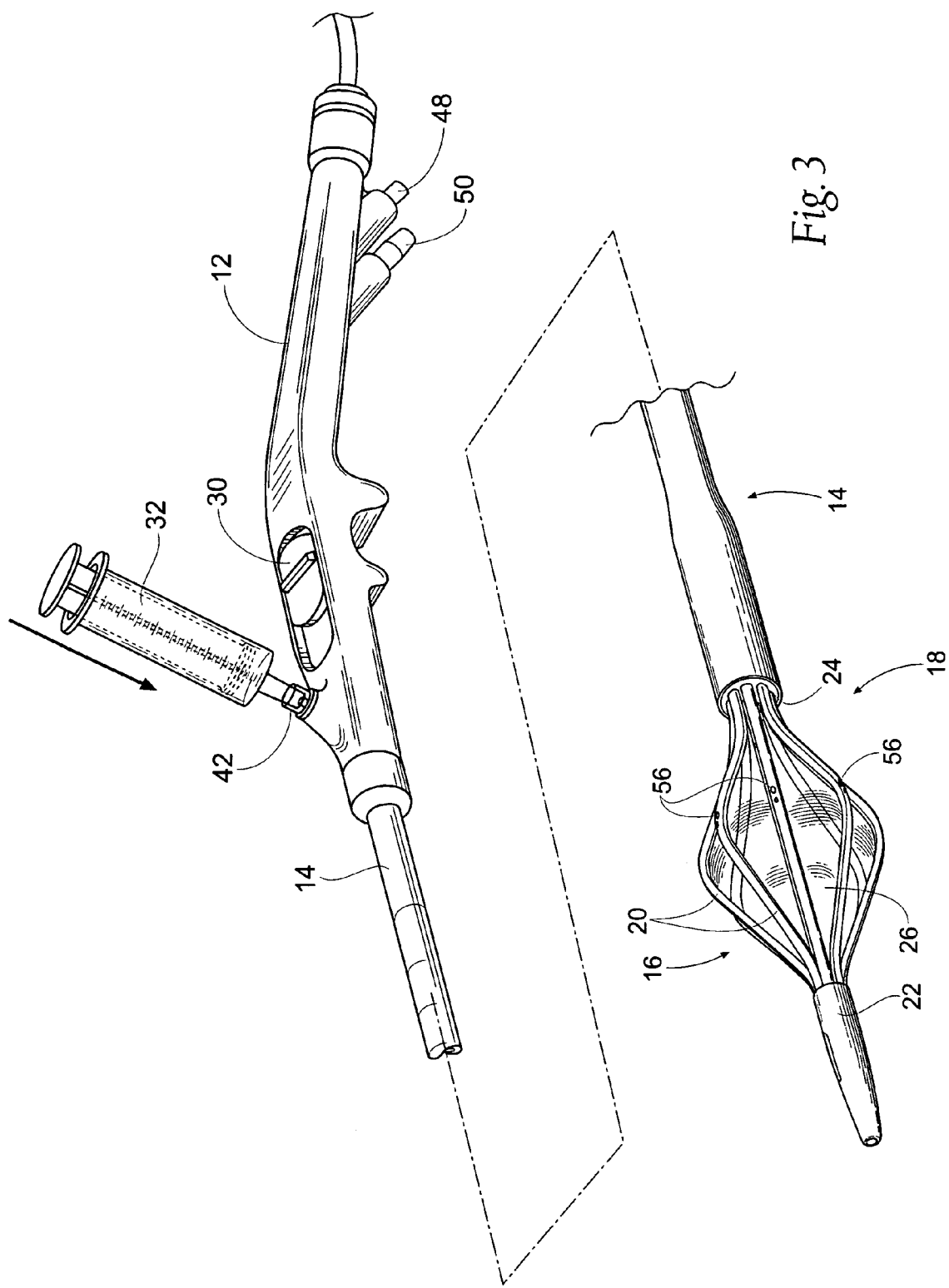
FIG. 3 is an enlarged view of the treatment device shown in FIG. 2, with the basket expanded due to inflation of interior balloon structure and the electrode elements still retracted.
Figure 4:
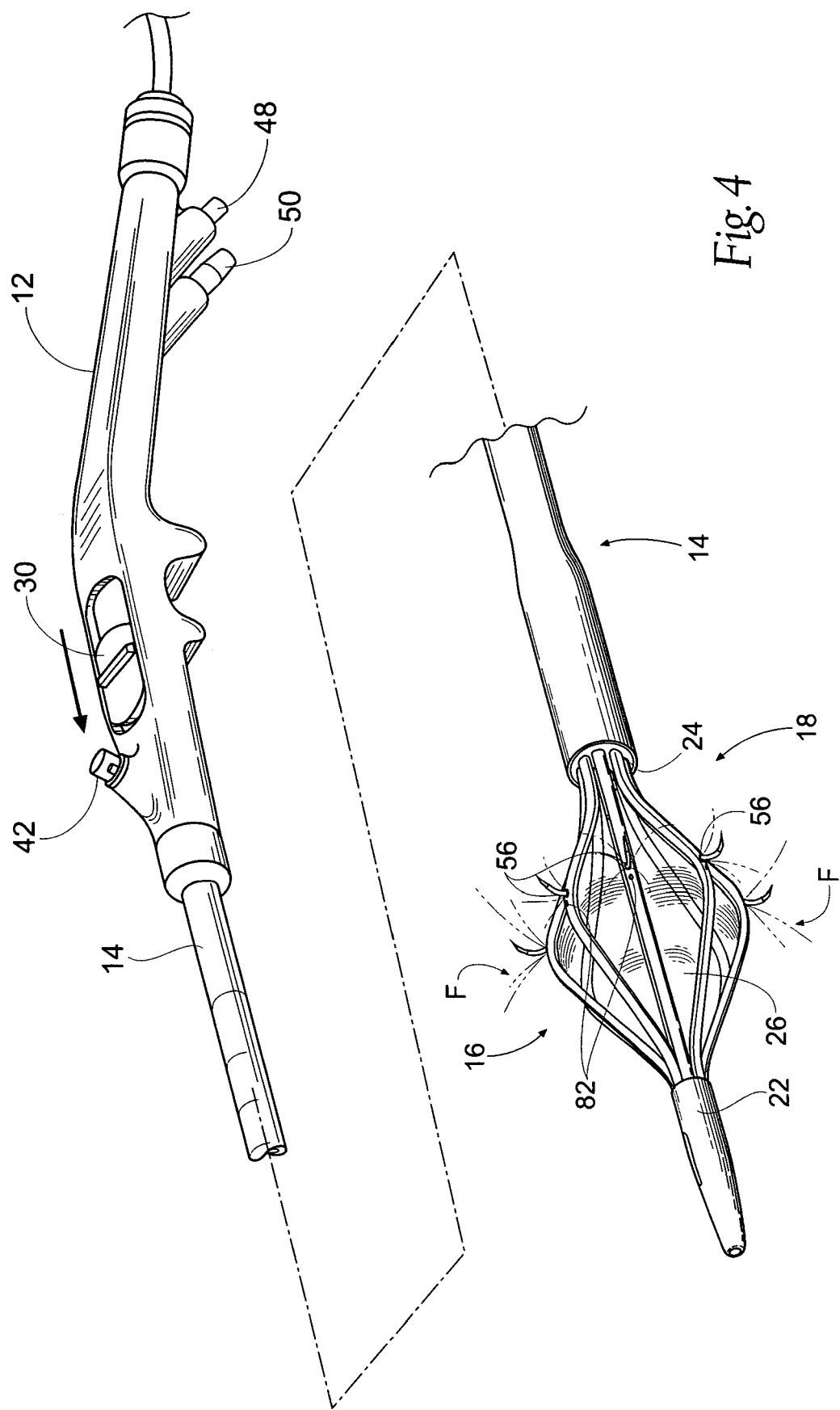
FIG. 4 is an enlarged view of the treatment device shown in FIG. 2, with the basket expanded due to inflation of interior balloon structure and the electrode elements extended for use, FIG. 4 also showing the passage of irrigation fluid from the basket to cool the surface tissue while radio-frequency energy is applied by the electrode elements to subsurface tissue.

In the embodiment shown in FIGS. 2 to 4, the operative element 16 comprises a three-dimensional basket 18. The basket 18 includes an array of arms 20. The arms 20 are desirably made from extruded or molded plastic, but they could also be formed from stainless steel or nickel titanium alloy. As shown in FIG. 2, the arms 20 are assembled together between a distal tip 22 and a proximal base element 24.

As FIGS. 3 and 4 show, an expandable structure 26 comprising, e.g., a balloon, is located within the basket 18. The expandable balloon structure 26 can be made, e.g., from a Polyethylene Terephthalate (PET) material, or a polyamide (non-compliant) material, or a radiation cross-linked polyethylene (semi-compliant) material, or a latex material, or a silicone material, or a C-Flex (highly compliant) material. Non-compliant materials offer the advantages of a predictable size and pressure feedback when inflated in contact with tissue. Compliant materials offer the advantages of variable sizes and shape conformance to adjacent tissue geometries.

The balloon structure 26 presents a normally, generally collapsed condition, as FIG. 2 shows. In this condition, the basket 18 is also normally collapsed about the balloon structure 26, presenting a low profile for deployment into the targeted tissue region.

Expansion of the balloon structure 26, e.g., by the introduction of air through a syringe 32 coupled to a one-way check valve fitting 42 on the handle 12 (see FIG. 3), urges the arms 20 of the basket 18 to open and expand, as FIG. 3 shows. The force exerted by the balloon structure 26 upon the basket arms 20, when expanded, is sufficient to exert an opening force upon the tissue surrounding the basket 18.

Figure 5:
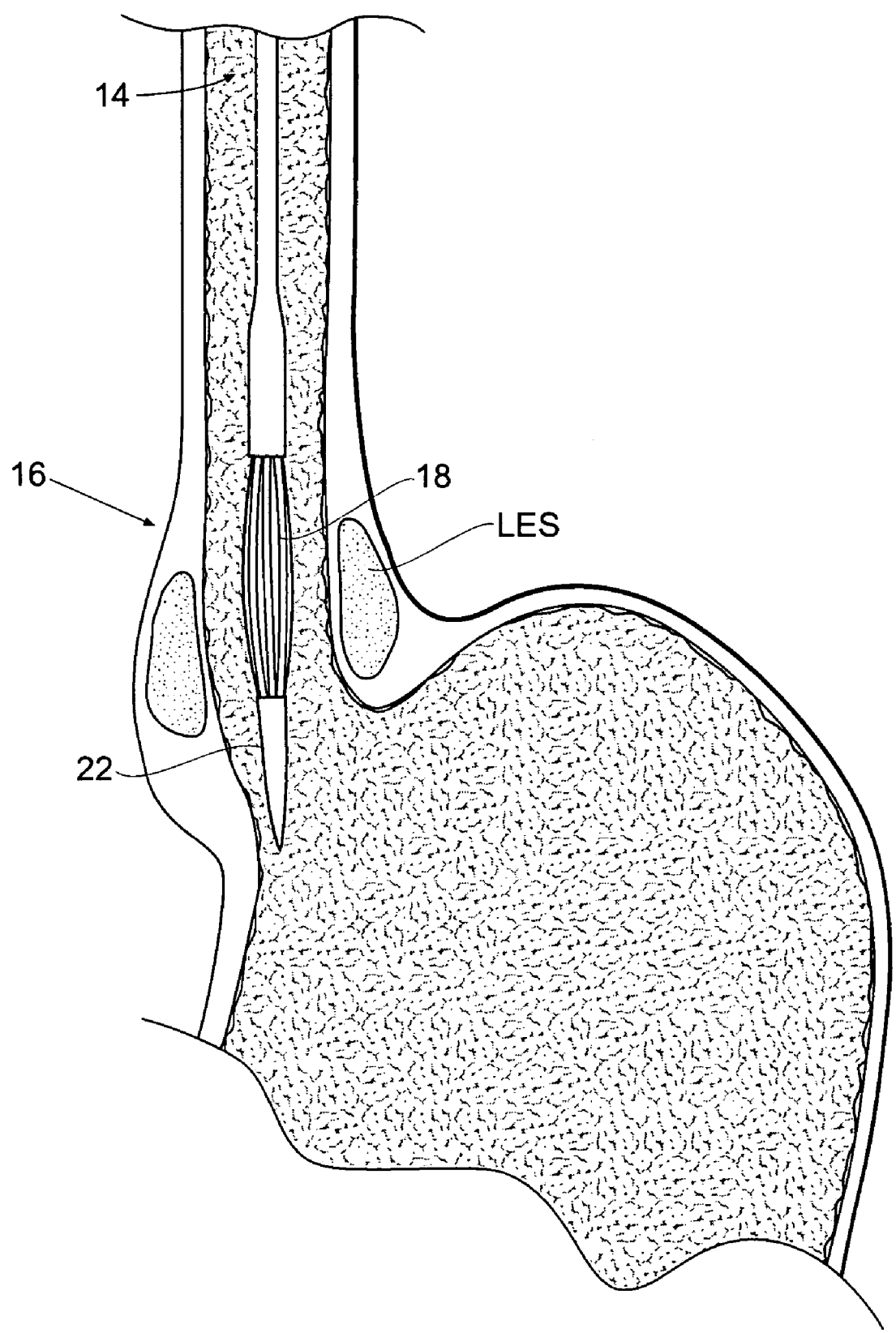
FIGS. 5 to 7 are simplified anatomic views showing the use of the treatment device shown in FIGS. 2 to 4 deployed in the region of the lower esophageal sphincter to form an array of lesions.
Figure 6:
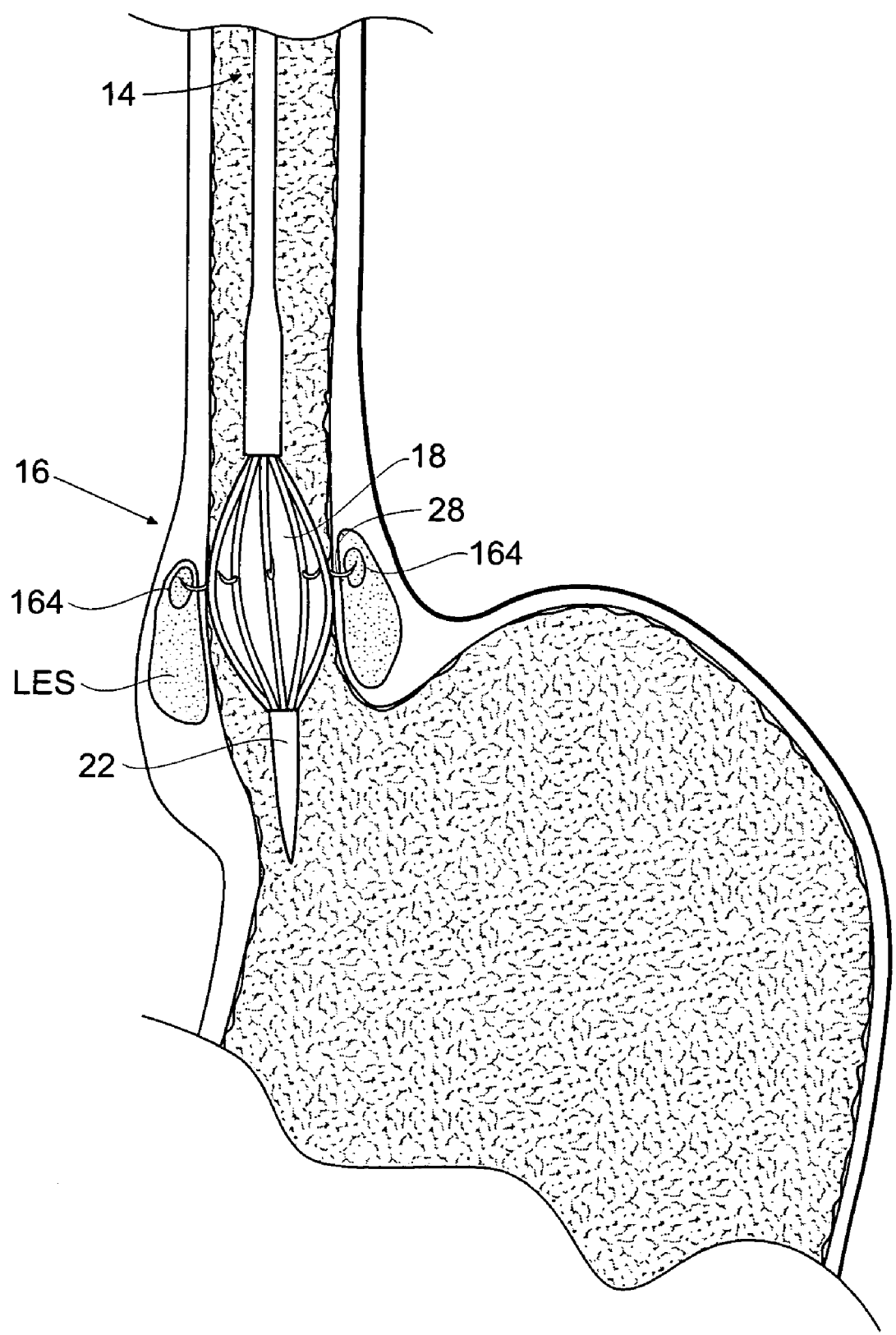

For the purpose of illustration (see FIGS. 5 and 6), the targeted tissue region comprises the lower esophageal sphincter (LES) and cardia of the stomach. When deployed in this or any sphincter region, the opening force exerted by the balloon structure 26 serves to dilate the sphincter region, as FIG. 6 shows.

Each basket arm 20 carries an electrode element 28. A push-pull lever 30 on the handle (see FIG. 4) is mechanically coupled through the catheter tube 14 to the electrode elements 28. In use, pushing and pulling on the lever 30 causes the electrode elements 28 to slide within the lumens in the basket arms 20 between a retracted position (shown in the FIG. 3) and an extended position (shown in FIG. 4). As FIG. 4 shows, the electrode element 28, when extended, projects through an opening 56 in the basket arm. When deployed in the tissue region (see FIG. 6), the extended electrode element 28 pierces tissue. As FIG. 4 shows, temperature sensing elements 82

(e.g., thermocouples) are desirably carried by the arms 20 near the electrode elements 28 to sense tissue temperature conditions.

In a desired arrangement, the electrode elements 28 deliver radio frequency energy, e.g., energy having a frequency in the range of about 400 kHz to about 10 mHz. A return path is established, e.g., by an external patch electrode, also called an indifferent electrode. In this arrangement, the application of radio frequency energy serves to ohmically heat tissue in the vicinity of the electrode elements 28, to thermally injure the tissue and form the localized sub-surface lesions 164, which are shown in FIG. 6. Of course, tissue heating can be accomplished by other means, e.g., by coherent or incoherent light; heated or cooled fluid; resistive heating; microwave; ultrasound; a tissue heating fluid; or cryogenic fluid.

In this arrangement, the natural healing of subsurface lesions or pattern of subsurface lesions created by the applied energy leads to a physical tightening of the sphincter and/or adjoining cardia and/or a reduction in the compliance of these tissues. The subsurface lesions can also result in the interruption of aberrant electrical pathways that may cause spontaneous sphincter relaxation. In any event, the treatment can restore normal closure function to the sphincter.

The electrode elements 28 can be formed from various energy transmitting materials. For deployment in the esophagus or cardia of the stomach, the electrode elements 28 are formed, e.g., from nickel titanium. The electrode elements 28 can also be formed from stainless steel, e.g., 304 stainless steel, or a combination of nickel titanium and stainless steel.

In this arrangement, the electrode element 28 may comprise a hybrid of materials comprising stainless steel for the proximal portion and nickel titanium alloy for the distal portion.

The exterior surface of each electrode element 28 can carry an electrical insulating material, except at its distal region, where the radio frequency energy is applied to tissue. The presence of the insulating material serves to preserve and protect the mucosal tissue surface from exposure to the radio frequency energy, and, thus, from thermal damage. The insulating material can comprise, e.g., a Polyethylene Terephthalate (PET) material, or a polyimide or polyamide material.

As FIG. 1 shows, the treatment device 10 desirably operates as part of a system 36. The system 36 includes a generator 38 to supply the treatment energy to the operative element 16. In the illustrated embodiment, the generator 38 supplies radio frequency energy to the electrodes 28. A cable 40 plugged into the handle 12 electrically couples the electrode elements 28 to the generator 38. Electrode supply wires pass through the catheter tube 14 from the handle to the electrode elements 28.

The system 36 can also include certain auxiliary processing equipment. In the illustrated embodiment, the processing equipment comprises an external fluid delivery or irrigation apparatus 44. In the illustrated embodiment, the fluid delivery apparatus 44 comprises an integrated, self priming peristaltic pump rotor that is carried on a side panel of the generator 38. Other types of non-invasive pumping mechanisms can be used, e.g., a syringe pump, a shuttle pump, or a diaphragm pump.

A luer fitting 48 on the handle 12 couples to tubing 34 to connect the treatment device 10 to the fluid delivery apparatus 44. Irrigation supply tubing in the catheter tube 14 conveys irrigation fluid through a lumen in each basket arm 20 for discharge through irrigation openings 56 (see FIG. 4) by or near the electrode elements 28. This provides localized cooling of surface tissue. In the illustrated embodiment, the irrigation fluid (designated F in FIG. 4) is discharged directly at the base of each electrode element 28. In this arrangement, the irrigation fluid is conveyed through the same basket arm lumen and is discharged through the same basket arm opening 56 as the electrode element 28. Of course, other irrigation paths can be used.

In this arrangement, the processing equipment desirably includes an aspiration source 46. Another luer fitting 50 on the handle 12 couples tubing to connect the treatment device 10 to the aspiration source 46. The aspiration source 46 draws irrigation fluid discharged by or near the electrodes 28 away from the tissue region. The aspiration source 46 can comprise, for example, a vacuum source, which is typically present in a physician's suite.

The system 36 also desirably includes a controller 52. The controller 52 is linked to the generator 38 and the fluid delivery apparatus 44. The controller 52, which preferably includes an onboard central processing unit, governs the power levels, cycles, and duration that the radio frequency energy is distributed to the electrodes 28, to achieve and maintain temperature levels appropriate to achieve the desired treatment objectives. In tandem, the controller 52 also desirably governs the delivery of irrigation fluid.

The controller 52 desirably includes an input/output (I/O) device 54. The I/O device 54, which can employ a graphical user interface, allows the physician to input control and processing variables, to enable the controller to generate appropriate command signals.

Figure 7:
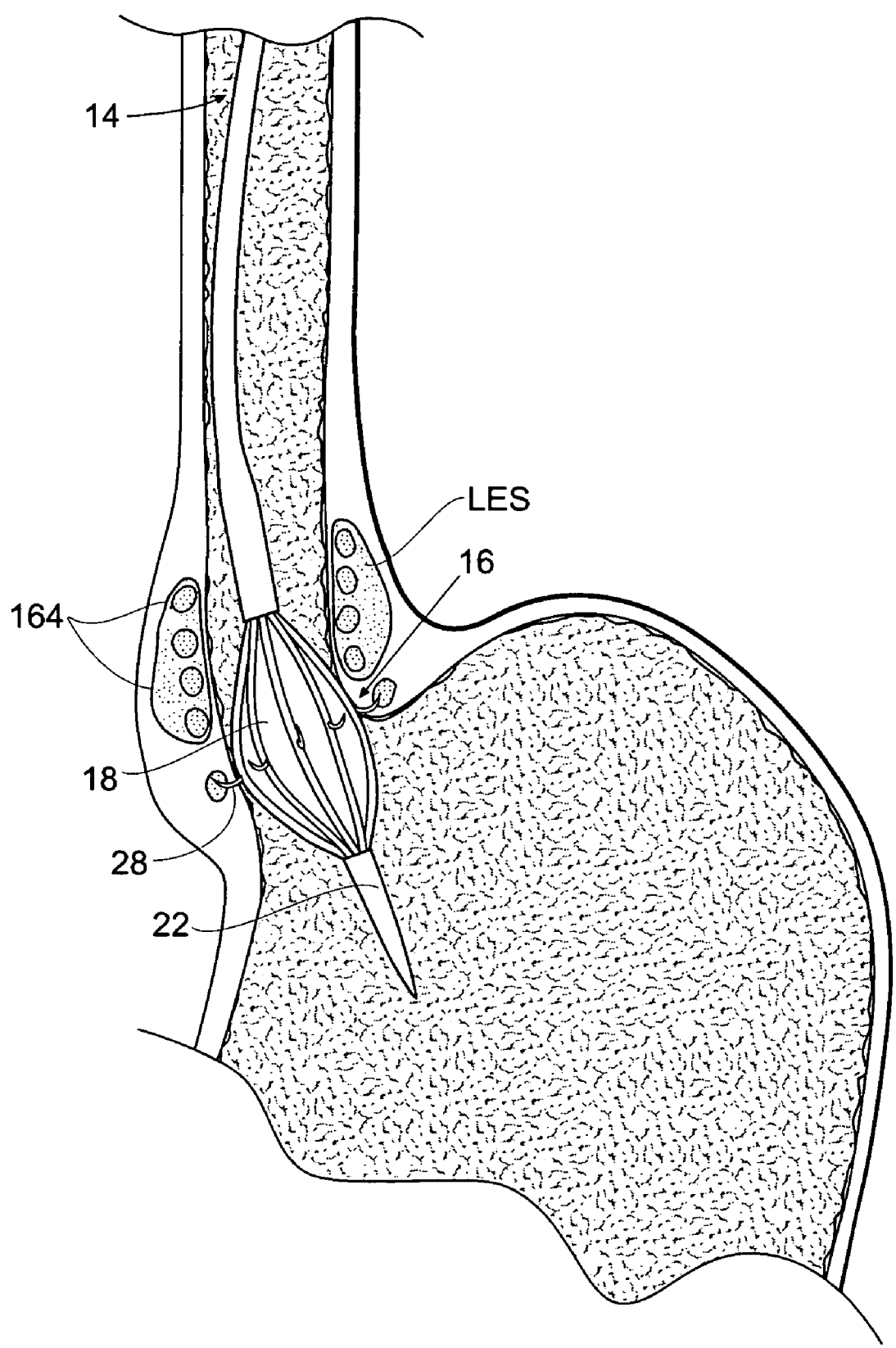

In use (see FIGS. 5 to 7), the operative element 16 can be deployed at or near the lower esophageal sphincter (LES) for the purpose of treating GERD. A physician can use the visualization functions of, e.g., an endoscope to obtain proper position and alignment of the operative element 16 with the LES.

Once proper position and alignment are achieved (see FIG. 6), the physician can expand the balloon structure 16 and extend the electrode elements 16 into piercing contact with tissue at or near the LES. Application of ablation energy forms the lesions 164. Retraction of the electrode elements 28 and collapsing of the balloon structure 16 allows the physician to reposition the operative element 16 and perform one or more additional ablation sequences (see FIG. 7). In this way, the physician forms a desired pattern of circumferentially and axially spaced lesions 164 at or near the LES and cardia.

II. Positioning Based Upon Fluid Pressure Sensing

It is desirable to be able to confirm that the basket arms 20 are positioned at or near the targeted tissue region. Direct visualization can be used for this purpose. In addition, or alternatively, electrode impedance can also be electrically sensed by the controller 52. A reduction in electrode impedance reflects that the electrode element 28 rests in tissue, compared to when the electrode element 28 is not in contact with tissue.

Alternatively, or in combination, the system 36 can include means 58 for assessing position based upon sensed changes in tissue pressure in and surrounding a targeted tissue region. The changes in tissue pressure are sensed based upon changes in pressure of a fluid (e.g., air or liquid) that is conveyed at or near the surface of the operative element 16 where tissue contact is intended. The means 58 includes means for causing a fluid subject to a pressure to flow in a path that has an outlet located at or near a surface of the operative element 16 intended to make tissue contact. Tissue pressure encountered at or near the path outlet affects pressure exerted on the path outlet and governs fluid flow in the path to varying degrees. The correlation between increases in tissue pressure encountered at or near the path outlet and fluid flow through the path gives rise to increases in fluid pressure within the path. The means 58 includes means for sensing a fluid pressure in the path. An increase in the prevailing fluid pressure sensed over time correlates with the presence of higher tissue pressures at or near the path outlet. The means 58 makes possible the sensing of the location of a remote structure relative to a targeted tissue region without direct or indirect visualization, or without other complicated electrical or mechanical paraphernalia.

In the illustrated embodiment, the high pressure zone created by the lower esophageal sphincter is a marker for the targeted tissue region. By sensing the pressure at which fluid is delivered at a slow rate through ports on the basket arms 20 while moving the basket structure 18 through the esophagus, the increased tissue pressure in the high pressure zone can be detected as the ports move through the zone.

In the illustrated embodiment (see FIG. 1) the means 58 includes a pressurized source 60 of air and a manometer 62. The air source 60 and manometer 62 can be part of the controller 52, or separate components coupled to the system 36, as FIG. 1 shows. Of course, the source 60 can provide a fluid other than air, in which case the manometer 62 would comprise a device that would sense the prevailing pressure of the selected fluid.

As shown in FIG. 1, the air source 60 and manometer 62 are coupled by tubing 64 to the irrigation supply tubing 34, which leads to the device 10. An inline valve 66 controls communication between the air source 60 and the tubing 34. When the valve 66 is opened, pressurized air from the source 60 is conveyed through the irrigation lumens in the basket arms 20, where they exit through the outlets 56. The flow of pressurized air through this path does not occur when the valve 66 is closed. In this way, pressurized air can be selectively conveyed through the lumen or lumens when it is desired to assess the location of the basket structure 18 relative to the high pressure zone of the lower esophageal sphincter. The manometer 62 senses the air pressure prevailing in the air path 64 and provides an output reflecting the magnitude of the sensed pressure.

Figure 8:
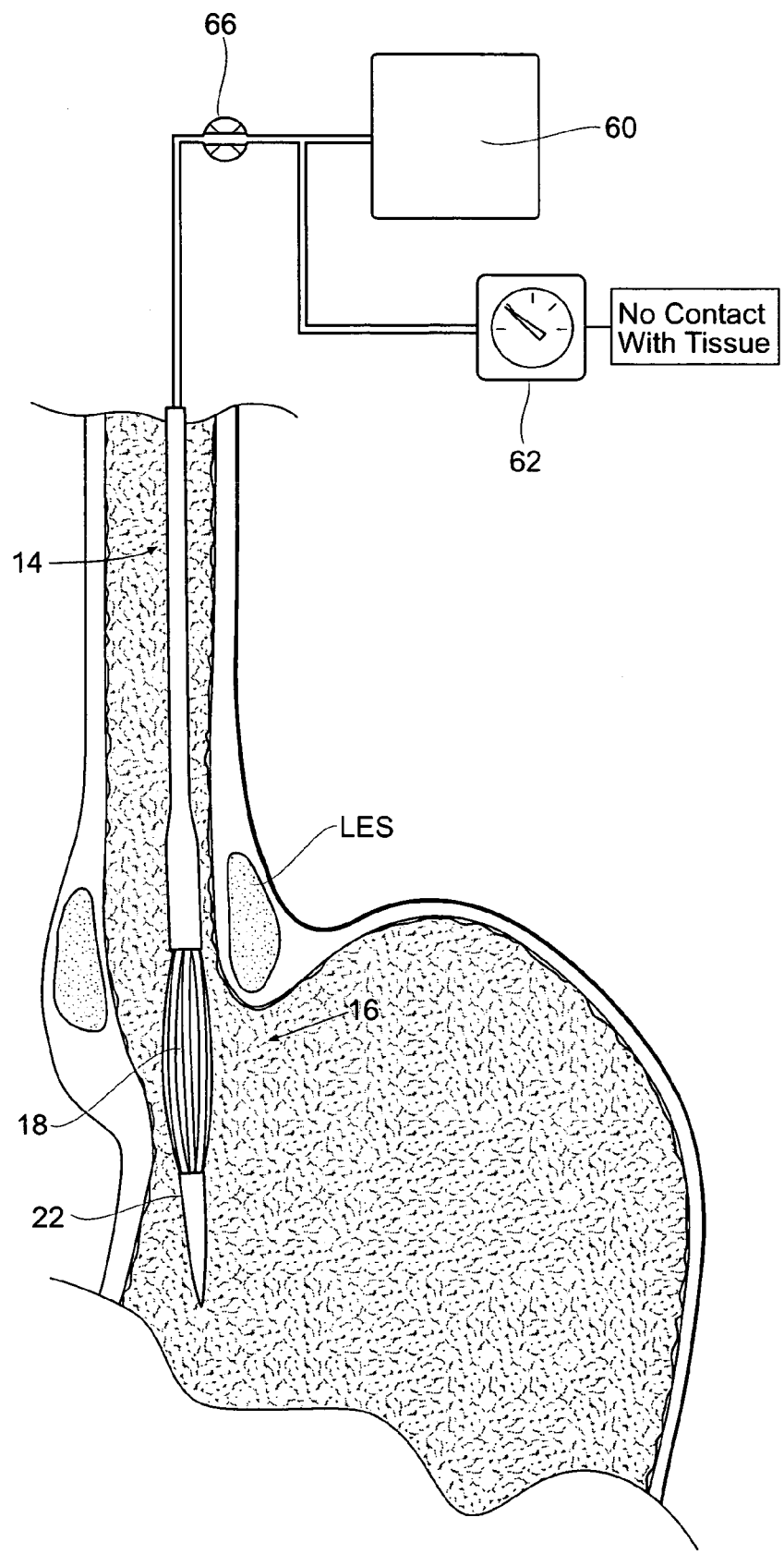
FIGS. 8 and 9 show, in simplified anatomic and schematic views, a system and method for sensing the position of the treatment device shown FIGS. 2 to 4 with respect to a targeted tissue region, by sensing fluid pressure in a fluid path having an outlet located at or near the electrode elements.

In use (see FIG. 8), the basket structure 18 is advanced while in a collapsed condition to a location beyond the targeted high tissue pressure zone, which in the illustrated embodiment, is the LES. While the basket structure 18 remains in a collapsed condition, the valve 66 is opened to place the pressurized air source 60 into communication with the irrigation lumens in the basket arms 20. Pressurized air is conveyed through the lumens, exiting through the openings 56. The manometer 62 will register a prevailing line pressure.

Figure 9:
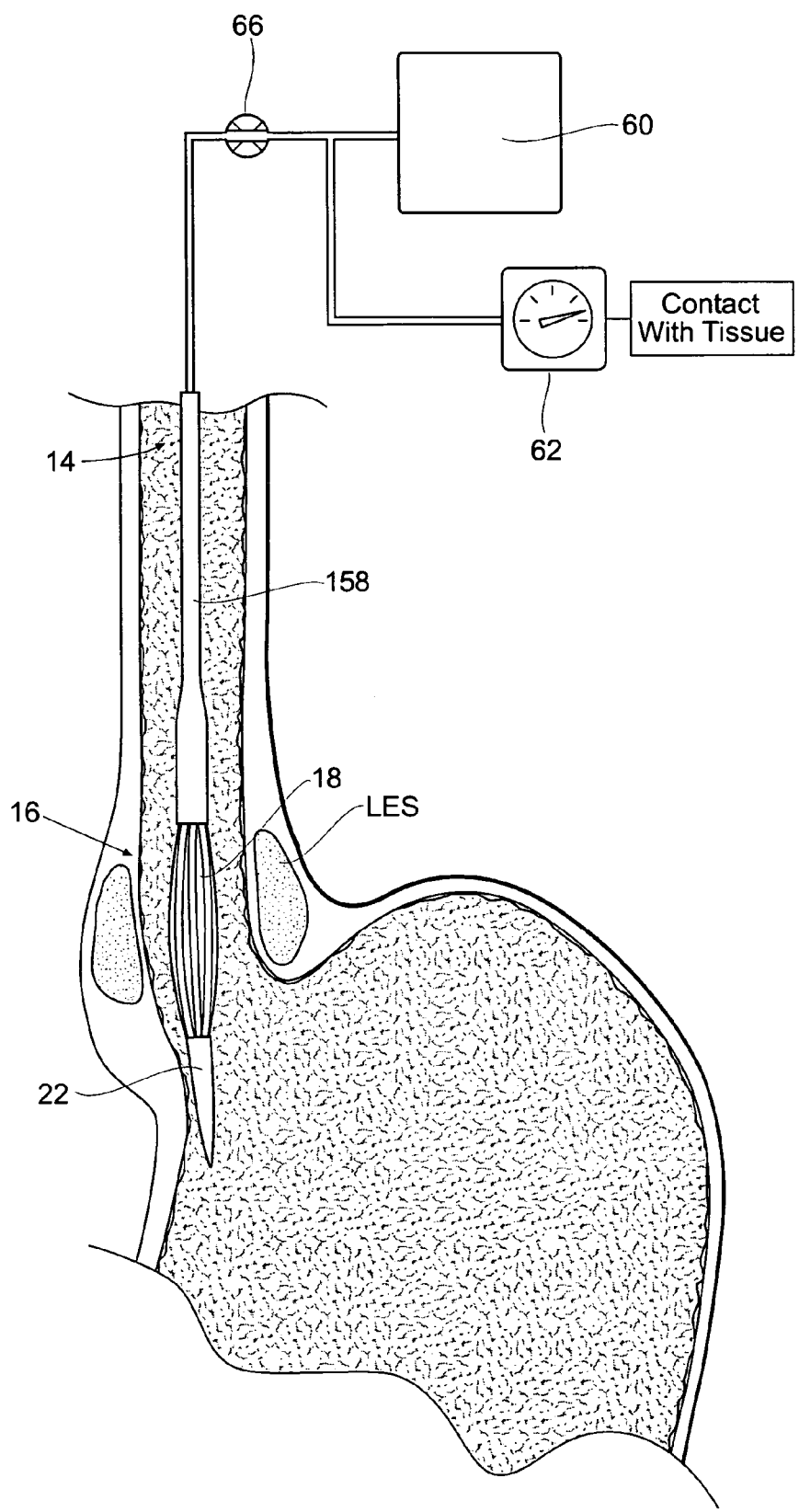

With the flow of air established, and with the basket structure 18 still collapsed, the physician draws the basket structure 18 back (see FIG. 9). The region of the basket structure 18 where the electrodes 28 are carried will eventually be brought into the high pressure zone. The increased tissue pressure in this region will impede air flow through the outlet openings 56 and generating a backpressure in the air path 64. As FIG. 9 shows, the manometer 62 will register an increase in sensed pressure. As the physician continues to draw the basket structure 18 back, above the high pressure zone, the sensed pressure will decrease accordingly. The localized increase in sensed pressure can thus be pin-pointed, which indicates that the electrode region of basket structure 18 is in the high tissue pressure zone and thereby positioned for use. The physician turns the valve 66 off.

Using reference marks on the catheter tube 14, the high pressure zone can be marked relative to an external anatomic reference, such as a bite block worn by the patient. Since the outlet ports 56 are coincident with the needle electrode locations, the exact location for delivery of radiofrequency energy is located in this way, without the need for endoscopy (or as an adjunct to endoscopy). The physician expands the basket structure 18 and proceeds with the lesion formation sequence.

The controller 52 can communicate with the manometer 62 (as shown in phantom lines in FIG. 1). In this arrangement, the controller 52 can be pre-programmed, e.g., to dynamically display the sensed pressure on the GUI 54 and/or to generate a visual and/or audible output when a threshold pressure indicative of tissue contact is sensed.

It should be appreciated that the manometer 62 and air pressure source 60 could, alternatively, be coupled to the aspiration supply line. Still alternatively, the manometer 62 can be carried on board the treatment device 10 itself, e.g., in the handle 20.

III. Controlling Pressure in the Balloon Structure

It is desirable to establish some control mechanism to assure that the balloon structure 26 is not over-inflated or otherwise subject to over-pressure conditions. This avoids damage to the balloon structure 26, as well as potential injury or trauma to tissue near or in contact with the balloon structure 26.

A. Tactile Control

Figure 10:
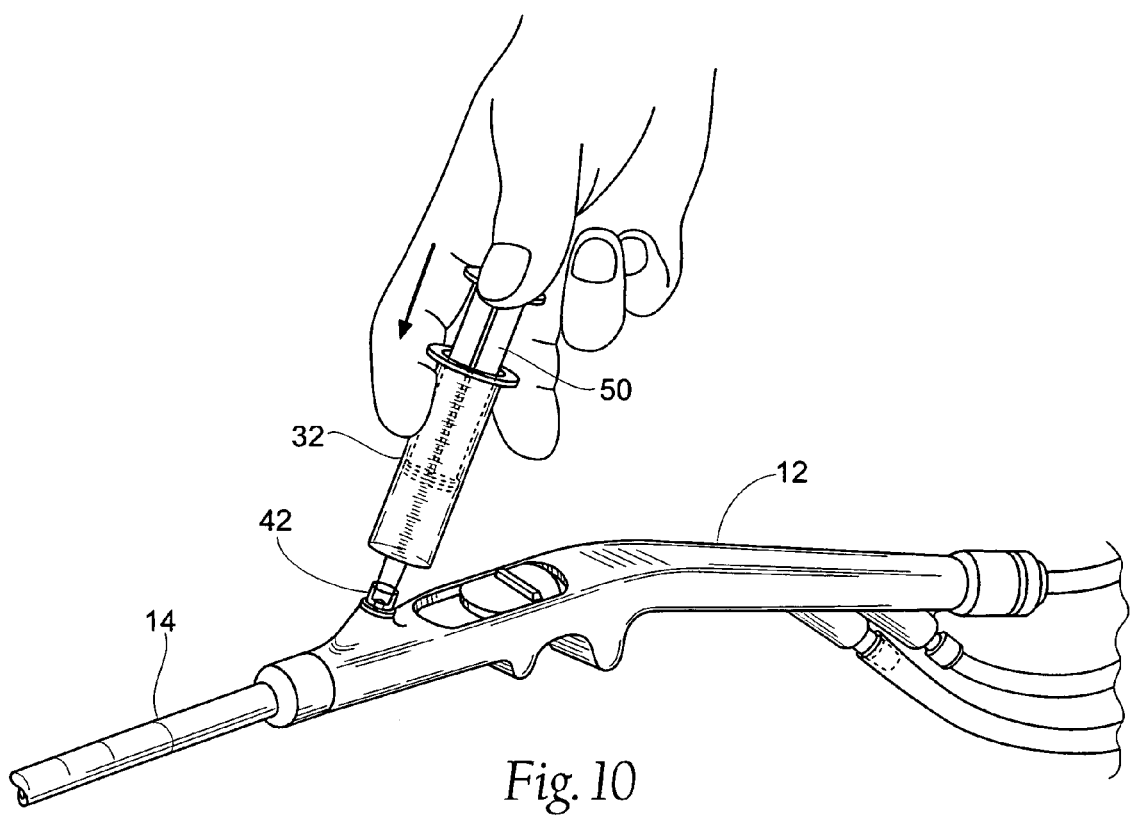
FIGS. 10 to 13 show, in perspective views, a system and method for manually inflating the balloon structure in the treatment device shown in FIGS. 2 to 4 while tactilely monitoring the magnitude of the inflation pressure to avoid over-inflation of the balloon structure.
Figure 11:
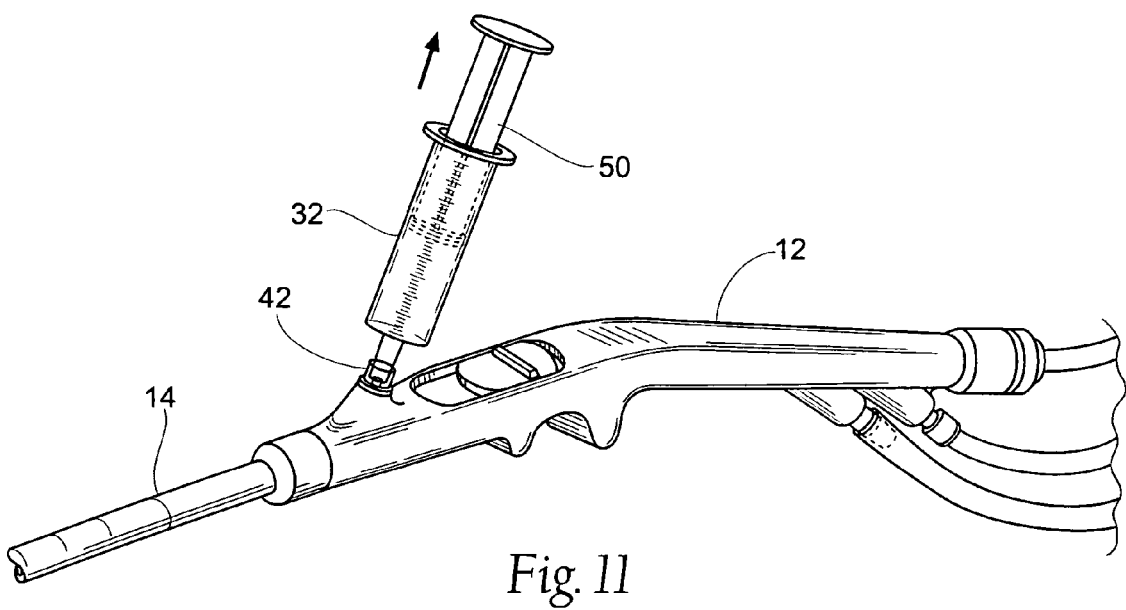
Figure 12:
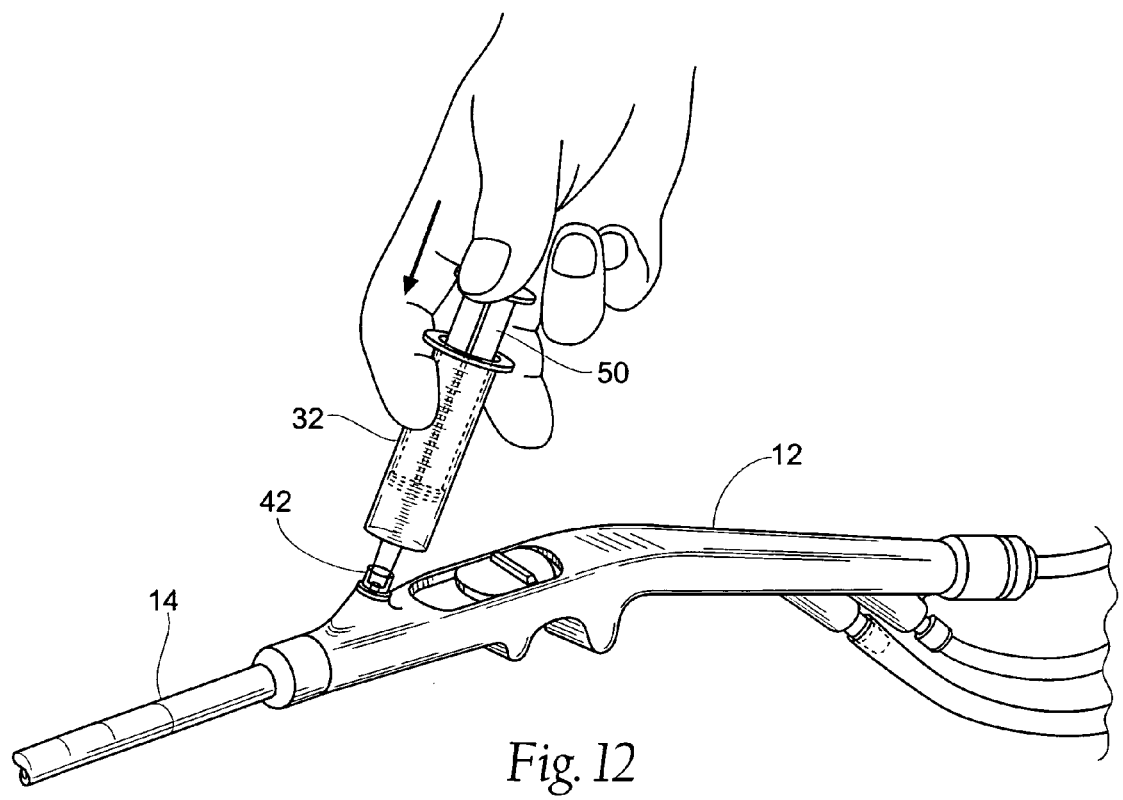
Figure 13:
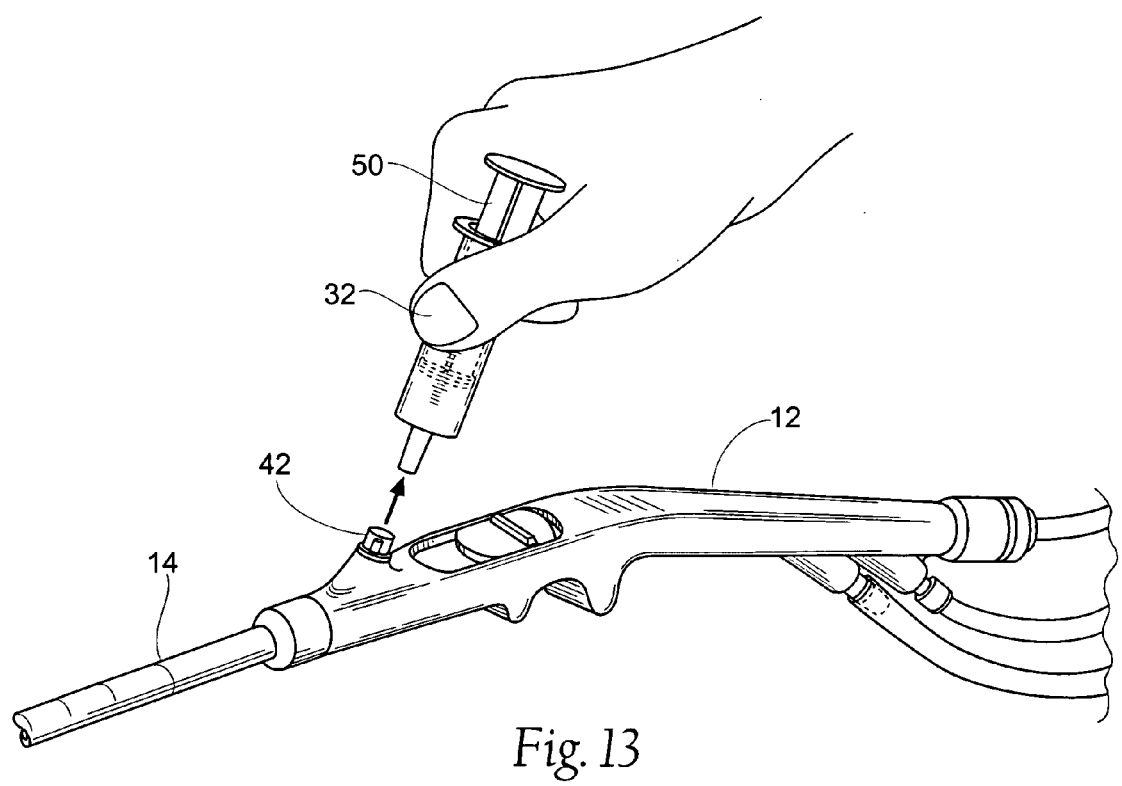

In one embodiment (see FIGS. 10 to 13) tactile feedback can be used. In this arrangement, a syringe 32 pre-filled with a pre-established volume of air (e.g., 25 cc) (see FIG. 10) is coupled to the one way check valve 42 on the handle. The physician depresses the plunger 50 of the syringe 32 to introduce air from the syringe 32 onto the balloon structure 26. The pre-filled volume of air in the syringe 32 is empirically selected based upon the size and physical properties of the balloon structure 26. As the balloon structure 26 approaches its desired interior pressure, the physician will tactilely feel progressive resistance to advancement of the plunger 50. When the balloon structure 26 is at the desired interior pressure, releasing the plunger will allow a finite back flow volume of air from the balloon structure 26 into the syringe 32 (e.g., 3-4 cc) (see FIG. 11). As FIG. 11 shows, the push back volume displaces the plunger 50 by a finite amount, providing the physician with direct visual and tactile feedback that the balloon structure 26 has been properly inflated. When plunger push back is observed, the physician responds by advancing the plunger 50 to replace the push back volume (as FIG. 12 shows), placing the balloon structure 26 at its desired inflation pressure. The physician disconnects the syringe 32 from the one-way check valve 42 (as FIG. 13 shows), which thereafter maintains the desired interior pressure in the balloon structure 26.

B. Pressure Relief Valve

In another embodiment (see FIG. 14), a pressure relief valve 68 may be coupled in line with the syringe 32 to the one-way valve fitting 42. The valve 68 is condition to open and vent the inflation fluid (in this case, air) at a predetermined pressure, which is selected to be the desired interior pressure of the balloon structure 26.

Figure 15:
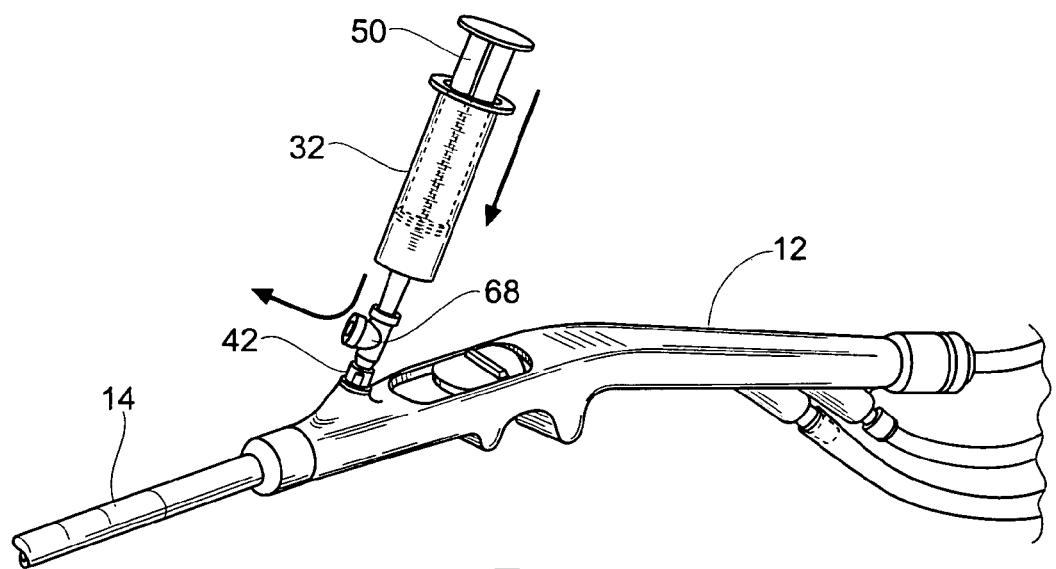

In this arrangement, the relief valve 68 remains closed as the syringe 32—pre-filled with a pre-established volume of air as already described—is manipulated to convey air into the balloon structure 26, until the balloon structure 26 reaches the predetermined desired interior pressure. At this time (see FIG. 15), the relief valve 68 will open, releasing excess air and venting additional air delivery by the syringe 32. In this way, further increase in interior pressure within the balloon structure 26 is actively prevented.

Figure 14:
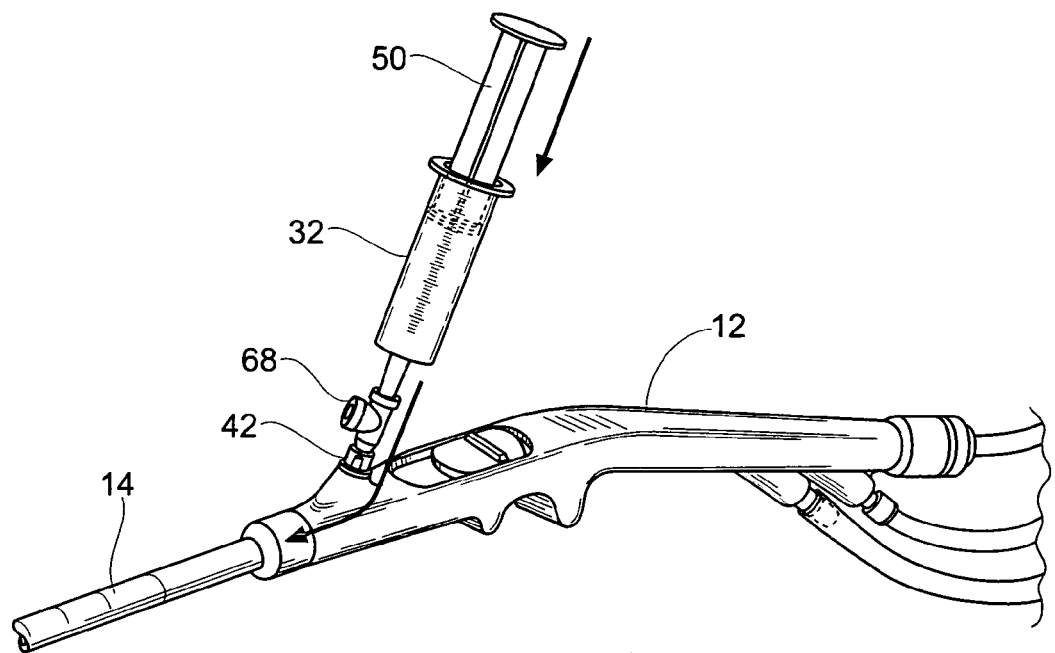
FIGS. 14 and 15 show, in perspective views, a system and method for manually inflating the balloon structure in the treatment device shown in FIGS. 2 to 4 while using a pressure relief valve to avoid over-inflation of the balloon structure.

The relief valve 68 can be located within the handle 12 or otherwise carried by the device 10. Alternatively, the relief valve 68 can be located in or on the supply line, as FIG. 14 shows. Still alternatively, the relief valve can be an integrated part of the controller 52, coupled by a sensing line to the device 10.

C. Real Time Pressure Monitoring

It may be desirable to dynamically monitor the magnitude of pressure within the balloon structure 26. For example, different pressure magnitudes may be desired at different locations in the tissue region where the pattern of lesions 164 is formed. In this embodiment, the system 36 includes means 70 for dynamically sensing the magnitude of pressure within the balloon structure 26.

In the illustrated embodiment (see FIG. 16), the means 70 comprises a pressure transducer 70. The pressure transducer 70 can be carried in the handle 20 of the treatment device 10 (as FIG. 16 shows), or it can be integrated into the controller 38.

Figure 16:
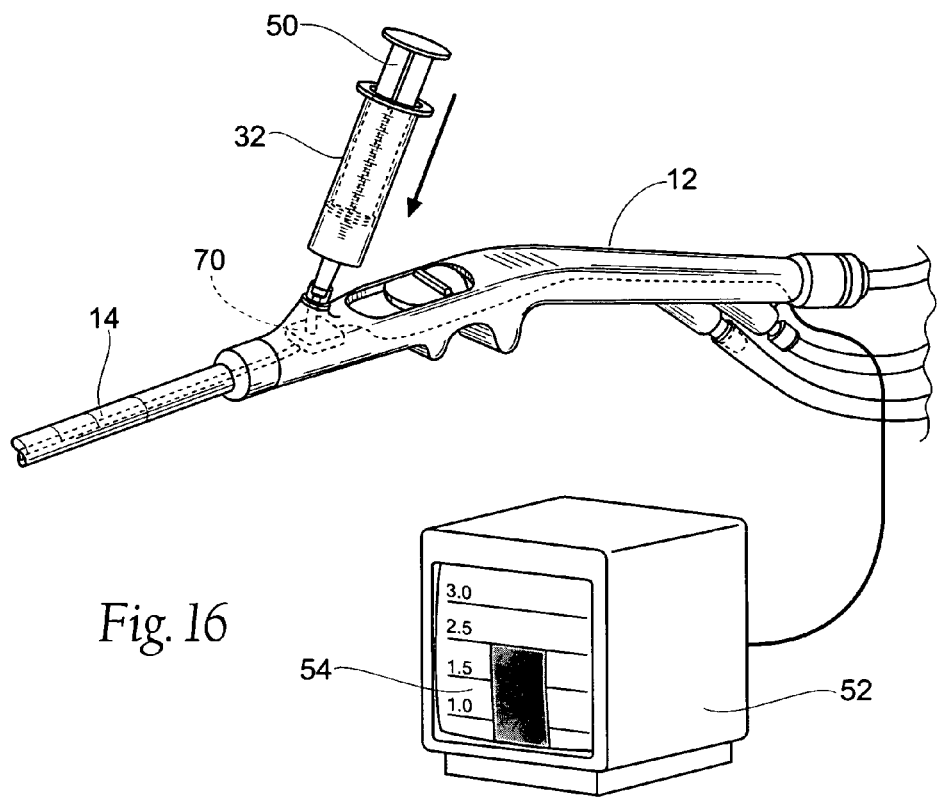
FIG. 16 shows, in a perspective view, a system and method that inflate the balloon structure in the treatment device shown in FIGS. 2 to 4, while dynamically monitoring pressure conditions within the balloon structure in real time, with an appropriate output generated to provide visual or audible feedback to the operator, and/or provide automated process control feedback based upon the sensed pressure information.

As FIG. 16 shows, a pressure gauge coupled to the transducer (or a virtual gauge on the GUI 54, which FIG. 16 shows) can be used to display the sensed pressure in real time. The controller 52 can be programmed to impose maximum pressure limits and generate visual or audible alarm conditions based upon the sensed pressure.

Figure 17:
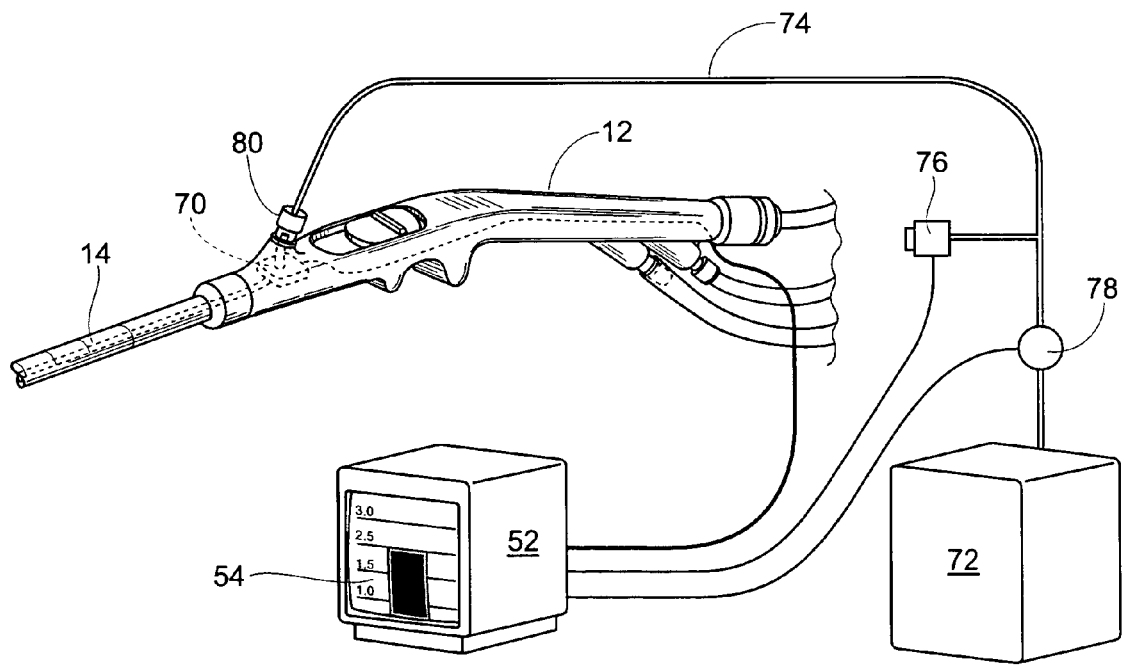
FIG. 17 shows, in a perspective view, a system and method that automatically inflate the balloon structure in the treatment device shown in FIGS. 2 to 4 by dynamically monitoring pressure conditions within the balloon structure.

With dynamic monitoring of pressure, the inflation of the balloon structure 26 can be placed under the control of the controller 52, and thereby automated. As FIG. 17 shows, the system includes a source 72 of fluid pressure, which can be air or a liquid like saline. The source 72 is coupled to the controller 52 and can be commanded to selectively supply inflation fluid under either positive or negative pressure. The source 72 is coupled via a supply line 74 to a supply fitting 80 on the handle 12. This arrangement replaces the use of a manual syringe and the one-way check valve 42.

The supply line 74 includes a control valve 78, which is coupled to the controller 52. The supply line 74 also includes a pressure relief valve 76, which is likewise coupled to the controller 52.

In use, upon positioning of the balloon structure 26 in a collapsed condition at or near the targeted tissue site, the controller 52 (e.g., in response to a foot switch operated by the physician) commands opening of the control valve 78. The controller 52 also commands the supply of the inflation fluid from the source 72 under positive pressure. The balloon structure 26 undergoes inflation.

The transducer 70 dynamically monitors the interior pressure as the balloon structure 26 inflates. The controller 52 compares the sensed pressure to a maximum threshold, which can be either preprogrammed in the controller 52 or based upon a selected input by the physician. The controller 52 can also be programmed to select the threshold pressure according to the current location of the balloon structure 26, which can be provided by input from the physician. When the sensed pressure reaches the selected maximum threshold, the controller 52 opens the pressure relief valve 76. Thereafter, the controller 52 toggles the pressure relief valve 76 open and closed to automatically maintain the desired interior inflation pressure at the threshold.

When it is desired to change the location of the balloon structure 26, or to withdraw the balloon structure 26, the controller 52 (e.g., in response to a foot switch operated by the physician) commands drawing negative pressure through the supply line 74 (while also closing the relief valve 76), to deflate the balloon structure 26. If, after repositioning, subsequent lesion formation is desired, the controller 52 (e.g., in response to a foot switch operated by the physician) can again command the supply of inflation fluid under positive pressure from the source 72, to again inflate the balloon structure 26 under the control of the transducer 70, as just described.

In this way, the system 36 serves to automatically control the inflation and deflation of the balloon structure 26, while keeping the balloon pressure within the prescribed limits.

Figure 18:
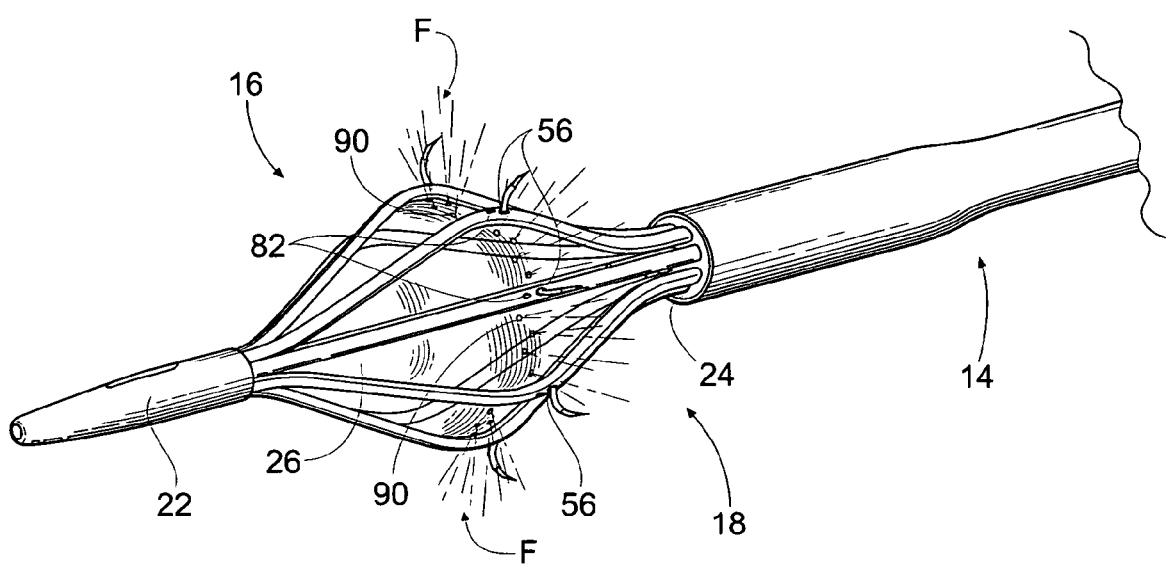
FIG. 18 is a perspective view of a treatment device comprising basket structure that carries selectively deployable electrode elements and that expands in response to inflation of an interior balloon structure with a liquid under the control of the system shown in FIG. 17, FIG. 18 showing the basket in an inflated condition with the electrode elements extended and the inflation liquid also serving as irrigation fluid discharged through an array of openings formed in the balloon structure.

The system 36 is particularly well suited for use in association with an operative element 18 as shown in FIG. 18. In this embodiment, the inflation fluid is a liquid that also serves as an irrigation fluid F. The irrigation fluid F is discharged in the vicinity of each electrode element 28 through an array of openings 90 formed in the balloon structure 18 itself. The openings 90 can be formed, e.g., by laser drilling, mechanical drilling, or poking with a hot needle. This arrangement eliminates the need for a dedicated irrigation passage and through openings in the basket arms 20. The inflation fluid thereby serves a dual purpose. First, the inflation fluid expands the basket structure 26 carrying the electrode elements 28, enabling their use. Second, the inflation fluid also serves as an irrigation fluid to cool the targeted tissue region. In this arrangement, the system 36 provides dynamic pressure monitoring and control of the inflation fluid and irrigation fluid, so that the requirements of simultaneous inflation of the balloon structure 18 and irrigation fluid delivery can be balanced, in order to inflate the balloon structure 18 to the desired pressure while achieving a desired irrigation fluid flow rate.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

We claim:

1. A method of forming a lesion pattern in submucosal tissue at or near a sphincter comprising providing a tissue treatment device comprising a catheter, an operative element carried by the catheter comprising a plurality of tissue-piercing energy delivery devices movable between a retracted position within the catheter and an extended position protruding from the catheter, an expandable member carried by the catheter adjacent the plurality of tissue-piercing energy delivery devices movable between a collapsed condition and an expanded condition, and a lumen adjacent the tissue-piercing energy delivery devices to convey fluid, preparing the tissue treatment device for deployment at or near a sphincter by placing the expandable member in the collapsed condition and placing the tissue-piercing energy delivery devices in the retracted position, advancing the catheter toward the sphincter until the tissue treatment device is located in a tissue region at or near the sphincter, coupling a source of air under pressure to the lumen, conveying air through the lumen at a pressure that varies according to proximity of the plurality of tissue-piercing energy delivery devices to tissue, manipulating the catheter while sensing variations in the pressure, wherein the sensed pressure increases with proximity of the plurality of tissue-piercing energy delivery devices to tissue, monitoring the variations in the pressure until a desired pressure condition is sensed indicative of positioning the plurality of tissue-piercing energy delivery devices at a desired treatment site at or near the sphincter, expanding the expandable member in the desired treatment site to exert an opening force upon tissue in the desired treatment site, moving the plurality of tissue-piercing energy delivery devices to the extended condition into submucosal tissue in the desired treatment site, delivering energy from the tissue-piercing energy delivery devices to produce a plurality of submucosal lesions in submucosal tissue comprising the lesion pattern at or near the sphincter, and coupling a source of cooling fluid to the lumen, and conveying the cooling fluid through the lumen to cool surface tissue adjacent the submucosal tissue.

2. A method according to claim 1
wherein advancing the catheter toward the sphincter until the tissue treatment device is located in a tissue region at or near the sphincter comprises advancing the tissue treatment device into a tissue region beyond the sphincter, and
wherein manipulating the catheter while sensing variations in the pressure comprises drawing the tissue treatment device back toward the sphincter.

3. A method according to claim 1
wherein sensing variations in the pressure includes using a manometer.

4. A method according to claim 1
wherein the sphincter includes the lower esophageal sphincter.

5. A method according to claim 1
wherein expanding the expandable member in the desired treatment site includes conveying air into the expandable member through a relief valve that prevents air conveyed into the expandable member reaching a preselected maximum pressure.

6. A method according to claim 1
wherein expanding the expandable member in the desired treatment site includes conveying air into the expandable member while monitoring pressure conditions within the expandable member.

7. A method according to claim 1
wherein radio frequency energy is delivered to produce the plurality of submucosal lesions.

\* \* \* \* \*